(12) United States Patent
Evans

(10) Patent No.: US 8,950,080 B2
(45) Date of Patent: Feb. 10, 2015

(54) CONTACT LENS CASE DRYING AND STORAGE RACK ASSEMBLY

(71) Applicant: Karen Marie Evans, Gilbert, AZ (US)

(72) Inventor: Karen Marie Evans, Gilbert, AZ (US)

( * ) Notice: Subject to any disclaimer, the term of this patent is extended or adjusted under 35 U.S.C. 154(b) by 85 days.

(21) Appl. No.: 13/893,700

(22) Filed: May 14, 2013

(65) Prior Publication Data

US 2013/0263466 A1    Oct. 10, 2013

Related U.S. Application Data

(63) Continuation-in-part of application No. 12/861,699, filed on Aug. 23, 2010, now Pat. No. 8,468,713.

(51) Int. Cl.
| | |
|---|---|
| F26B 25/18 | (2006.01) |
| F26B 25/00 | (2006.01) |
| A45C 11/00 | (2006.01) |
| F26B 9/00 | (2006.01) |
| F26B 9/10 | (2006.01) |
| A61L 12/00 | (2006.01) |

(52) U.S. Cl.
CPC ............... *F26B 25/00* (2013.01); *A45C 11/005* (2013.01); *F26B 9/003* (2013.01); *F26B 9/10* (2013.01); *A61L 12/00* (2013.01)
USPC .................................. 34/239; 34/511; 206/5.1

(58) Field of Classification Search
USPC .................. 34/511, 237, 239; 211/13.1, 85.1; 248/309.1; 206/5.1
See application file for complete search history.

(56) References Cited

U.S. PATENT DOCUMENTS

| | | |
|---|---|---|
| 3,124,240 A | 3/1964 | Croan |
| 3,623,492 A | 11/1971 | Frantz |
| D338,217 S | 8/1993 | Ives |
| D530,430 S | 10/2006 | Dunbar |
| 7,458,470 B2 | 12/2008 | Jerstroem |
| 7,832,551 B2 * | 11/2010 | Newman et al. ............... 206/5.1 |
| 2007/0125725 A1 | 6/2007 | Kemper |
| 2009/0065375 A1 | 3/2009 | Winters et al. |

* cited by examiner

*Primary Examiner* — Jiping Lu
(74) *Attorney, Agent, or Firm* — Michael W. Goltry; Robert A. Parsons; Parsons & Goltry

(57) ABSTRACT

A drying rack and contact lens storage case assembly consists of a contact lens storage case assembly that includes a base formed with externally threaded receptacles having inner diameters, and internally threaded caps having inner diameters and which relate to the respective receptacles. A drying frame is formed fingers that support pattern of lugs at openings through the frame. The lugs relate to inner diameters of the receptacles formed in the base and the caps, respectively. The receptacles are concurrently positionable on and over a pair of the patterns of lugs, the caps are concurrently positionable on and over another pair of the patterns of lugs, and the openings provide drying ventilation for the receptacles and the caps.

10 Claims, 7 Drawing Sheets

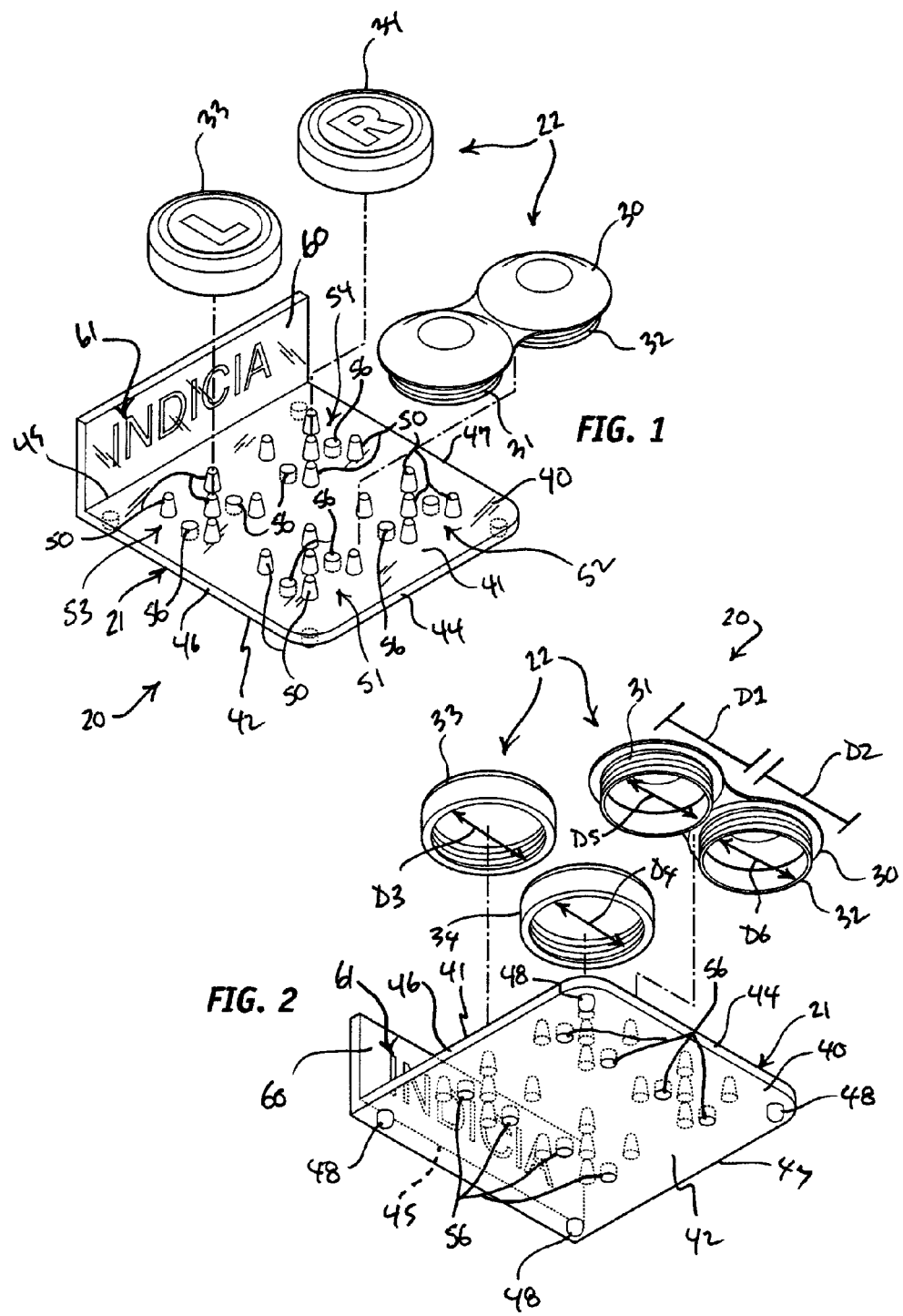

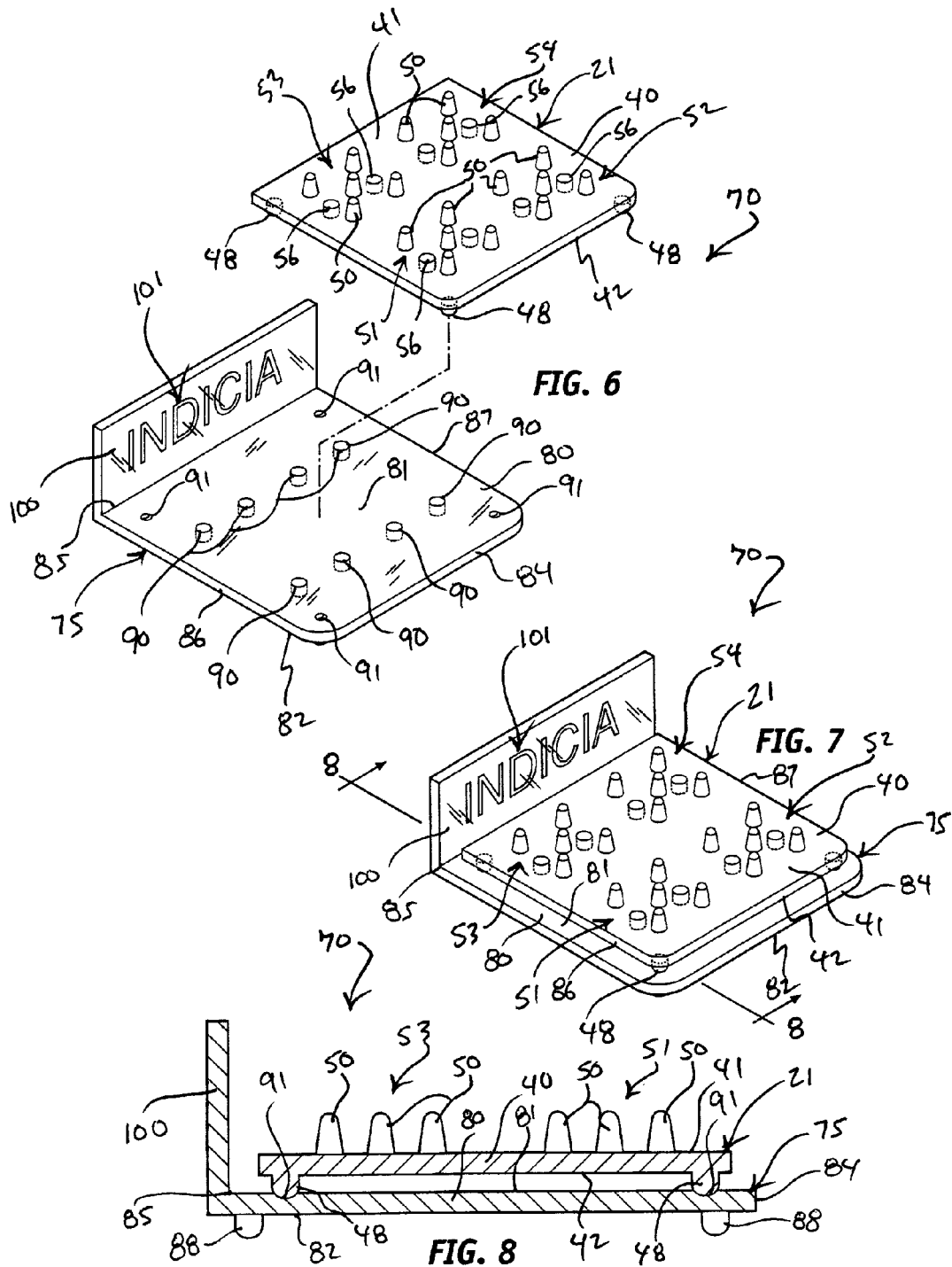

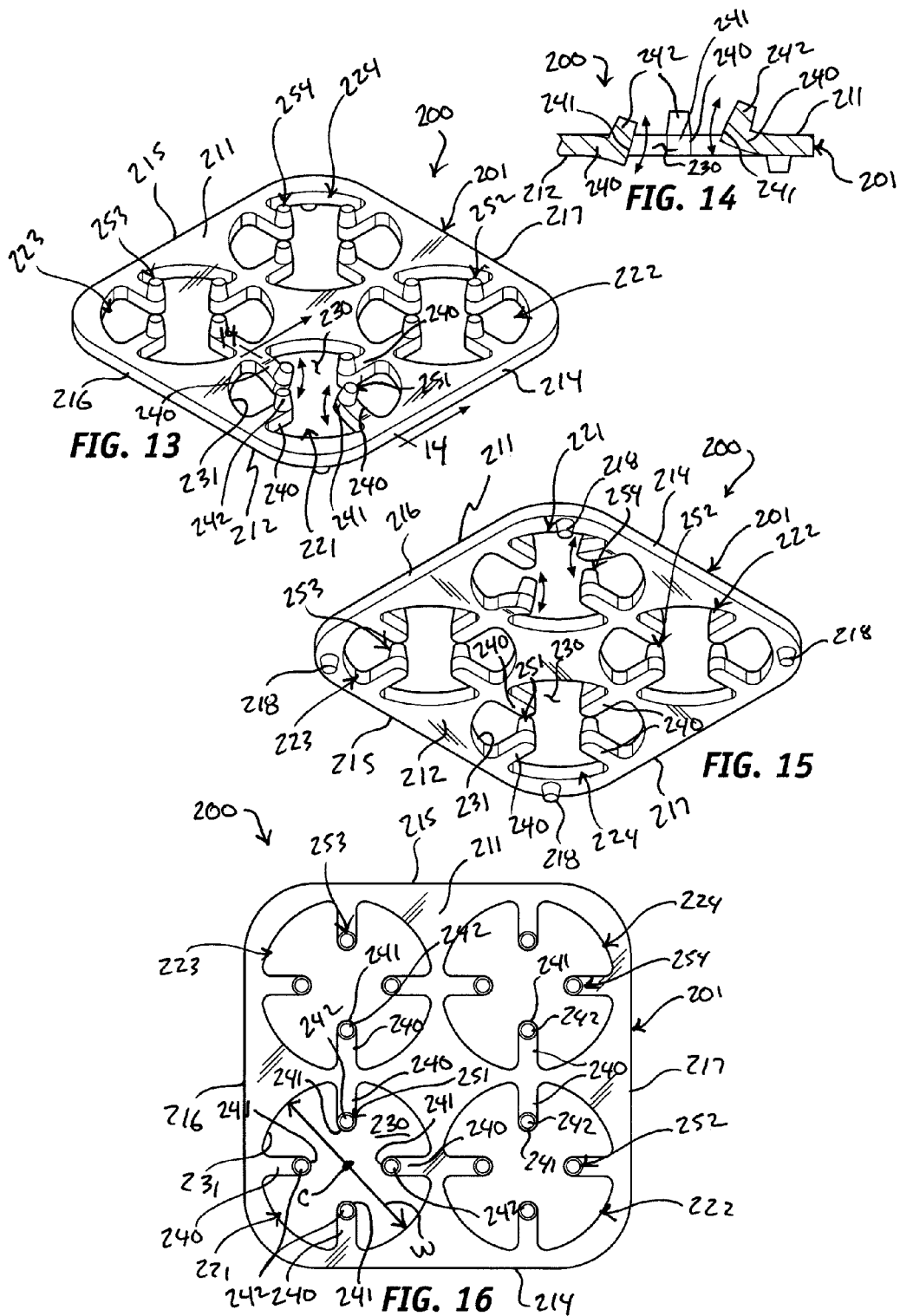

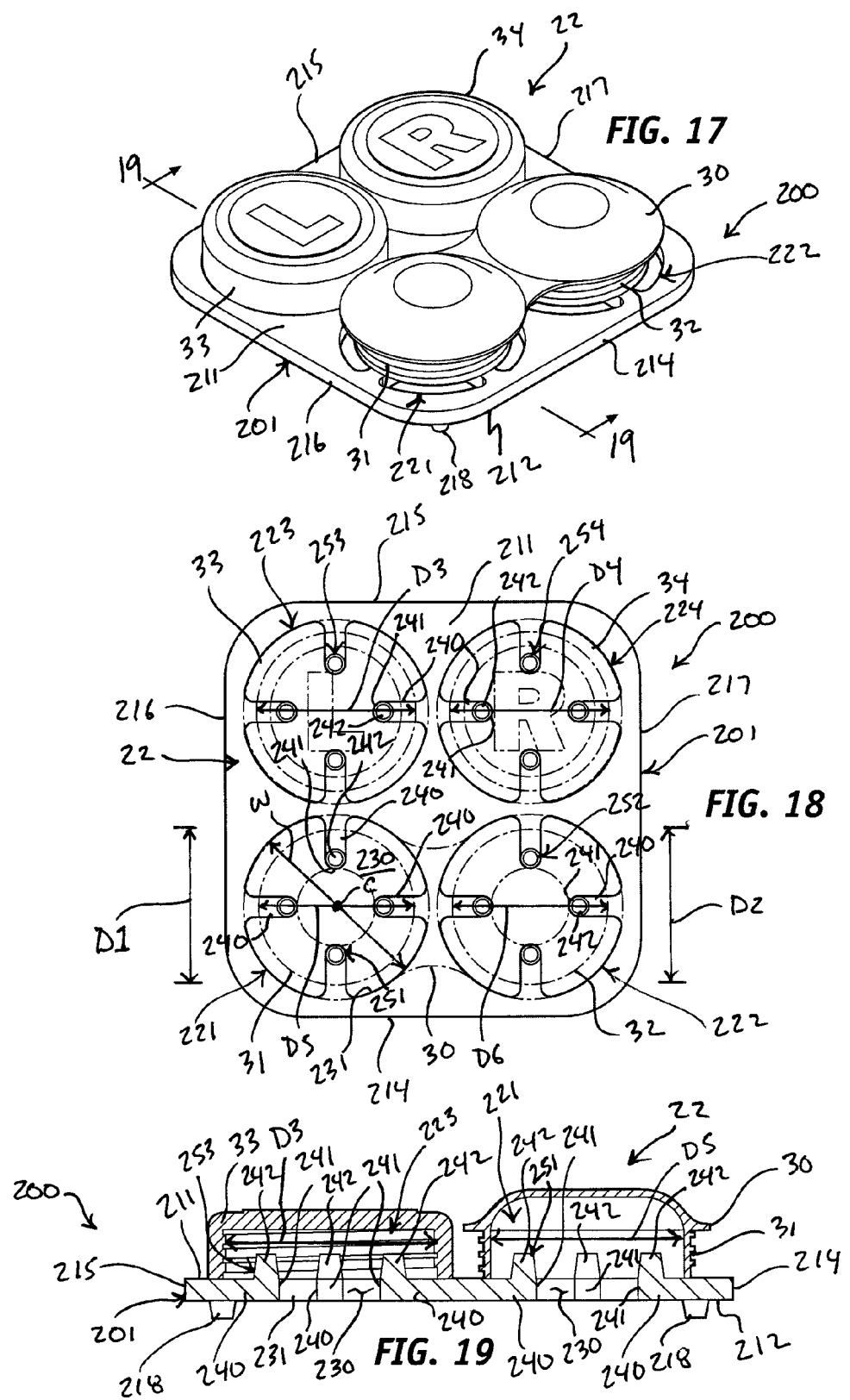

US 8,950,080 B2

CONTACT LENS CASE DRYING AND STORAGE RACK ASSEMBLY

FIELD OF THE INVENTION

The present invention relates to contact lens cases and covers and, more particularly, to systems and methods of drying and storing contact lens storage cases.

BACKGROUND OF THE INVENTION

Most contact lens wearers understand the importance of cleaning their contacts or contact lenses on a daily basis. Cleaning and disinfecting contacts on a daily basis extends the life of the contacts and reduces the risk of developing a potentially dangerous eye infection. A contact lens case, which is the "home" of the lenses during periods of nonuse, such as overnight, should be thought of as an extension of the contact lens, and should also be thoroughly cleaned on a regular basis.

Contacts lens cases can be a significant source of microbial contamination. To help prevent eye infections, contact lens cases should be cleaned, rinsed and properly dried every day, particularly after the contacts are removed from the case and placed in the eyes for the day.

Cleaning a contact lens case generally involves removing any solid matter or debris that may have fallen into the case, rinsing each section of the case, including the lids or caps, with the hot water or with same contact lens cleaning solution used to clean and disinfect the contacts. After cleaning, the contact lens case, including the lids or caps, must be thoroughly dried to prevent bacteria formation. Some people dry the sections of the contact lens case by wiping them with a dry cloth, or by placing the contact lens case components upside down on a clean towel. These drying techniques are generally not recommended because they can lead to microbial contamination that can, in turn, lead to painful eye infections. Furthermore, air-drying by simply placing the contact lens case components on a clean towel is often unsatisfactory as the towel does not provide a secure support for the components, which often leads to the contact lens case components falling to the floor or into the sink. Other people close the contact lens wet which does not allow for proper drying, or lay them flat on dirty bathroom counter or sink edge, both of which can lead to microbial contamination. If cases are laid open face up they are also slow to dry and are exposed to contaminants getting in such as dust, hairspray, germs, and the like. If the sections of the case are laid open face down on a flat surface they are substantially isolated from airflow to dry properly, which can also lead to microbial formation. Furthermore, in households where numerous people wear contact lenses, keeping each person's contact lens case components separate after cleaning and drying to prevent mismatching is particularly challenging, especially when they are cleaned at the same time.

SUMMARY OF THE INVENTION

According to the principle of the invention, a drying rack and contact lens storage case assembly includes a drying frame, and a contact lens storage case assembly. The contact lens storage case assembly consists of a base formed with first and second receptacles, and first and second caps relating to the first and second receptacles, respectively. The first and second receptacles are externally threaded, and the first and second caps of internally threaded. The first receptacle has a first inner diameter, and the second receptacle has a second inner diameter equal to the first inner diameter of the first receptacle. The first cap has a third inner diameter, and the second cap has a fourth inner diameter equal to the third inner diameter of the first cap. The third and fourth diameters of the first and second caps are each somewhat larger than each of the first and second diameters of the first and second receptacles, respectively. The drying frame has a lower face and an opposed upper face formed with opposed first and second patterns of protuberances relating to the first and second inner diameters of the first and second receptacles, respectively, and opposed third and fourth patterns of protuberances. The third pattern of protuberances relates to the third inner diameter of the first cap, and the fourth pattern of protuberances relates to the fourth inner diameter of the second cap. The first and second receptacles of the base of the contact lens storage case assembly are concurrently positionable on the first and second patterns of protuberances, the first cap is positionable on the third pattern of protuberances, and the second cap is positionable on the fourth pattern of protuberances, wherein the first pattern of protuberances is to extend into the first receptacle and is to be concurrently received against the first inner diameter of the first receptacle, the second pattern of protuberances is to extend into the second receptacle and is to be concurrently received against the second inner diameter of the second receptacle, the third pattern of protuberances is to extend into the first cap and is to be concurrently received against the third inner diameter of the first cap, and the fourth pattern of protuberances is to extend into the second cap and is to be concurrently received against the fourth inner diameter of the second cap. At least one ventilation opening is formed through the drying frame from the lower face to the upper face within each of the first, second, third, and fourth patterns of protuberances to provide drying ventilation. Supporting feet are formed in the lower face of the drying frame, which may be directed against a support surface to support the drying frame at an elevated location relative to the support surface.

The drying frame has a marginal perimeter edge encircling the first, second, third, and fourth patterns of protuberances. An upstanding support is attached to a length of the marginal perimeter edge. The support projects upward relative to the upper face of the drying frame, and there is identifying indicia carried by the support. In a particular embodiment, the identifying indicia are applied to a plate carried by the support. The plate is a separate and discreet component relative to the support, and is removably coupled to the support in a particular embodiment.

In the installation of the contact lens storage case assembly to the drying frame, the first and second receptacles of the base of the contact lens storage case assembly are concurrently deposited on the first and second patterns of protuberances, the first cap is deposited on the third pattern of protuberances, and the second cap is deposited on the fourth pattern of protuberances, wherein the first pattern of protuberances extends into the first receptacle and is concurrently received against the first inner diameter of the first receptacle, the second pattern of protuberances extends into the second receptacle and is concurrently received against the second inner diameter of the second receptacle, the third pattern of protuberances extends into the first cap and is concurrently received against the third inner diameter of the first cap, and the fourth pattern of protuberances extends into the second cap and is concurrently received against the fourth inner diameter of the second cap. Preferably, there is at least one ventilation opening formed through the drying frame from the lower face to the upper face within each of the first, second, third, and fourth patterns of protuberances providing drying ventilation for the first receptacle, the second receptacle, the first cap, and the second cap, respectively.

In yet a further embodiment, there is a support platform having a lower surface formed with supporting feet and an opposed upper surface formed with recesses arranged to concurrently accept the supporting feet formed in the lower face of the drying frame. The support platform has a marginal perimeter edge encircling the recesses formed in the upper surface of the support platform, an upstanding support is attached to a length of the marginal perimeter edge of the support platform, the support projects upward relative to the upper surface of the support platform, and identifying indicia is carried by the support. Ventilation openings are formed through the support platform from the lower surface to the upper surface to provide drying ventilation.

According to the principle of the invention, a drying rack and contact lens storage case assembly includes a contact lens storage case assembly consisting of an integral base formed with an externally threaded first receptacle having a first inner diameter and an opposed externally threaded second receptacle having a second inner diameter equal to the first inner diameter of the first receptacle, and internally threaded first and second caps relating to the first and second receptacles, respectively, the first cap having a third inner diameter, the second cap having a fourth inner diameter equal to the third inner diameter of the first cap, and the third and fourth diameters of the first and second caps each being somewhat larger than each of the first and second diameters of the first and second receptacles, respectively. A frame has opposed upper and lower faces. First, second, third, and fourth drying structures are formed in the frame. Each of the first, second, third, and fourth drying structures includes an opening formed through the frame from the upper face to the lower face, the opening having geometric center and a width greater than each of the first, second, third, and fourth inner diameters of the contact lens storage case assembly, and fingers formed in the frame, the fingers extending into the opening toward the geometric center and terminating with free ends located between the width and the geometric center of the opening, the free ends of each of the fingers formed with a lug projecting upwardly relative to the upper face of the frame, and the lugs being located between the width and the geometric center of the opening and residing in a region that is less than each of the first, second, third, and fourth inner diameters of the contact lens storage case assembly. The first and second receptacles of the base of the contact lens storage case assembly are concurrently positionable over the upper face of the frame on the fingers of the first and second drying structures, respectively, the first cap is positionable over the upper face of the frame on the fingers of the third drying structure, and the second cap is positionable over the upper face of the frame on the fingers of the fourth drying structure, wherein the lugs of the first drying structure are to extend into the first receptacle within the first inner diameter of the first receptacle, the lugs of the second drying structure are to extend into the second receptacle within the second inner diameter of the second receptacle, the lugs of the third drying structure are to extend into the first cap within the third inner diameter of the first cap, the lugs of the fourth drying structure are to extend into the second cap within the fourth inner diameter of the second cap, and the openings of the first, second, third, and fourth drying structures are to provide drying ventilation. The fingers of each of the first, second, third, and fourth drying structures are flexurally deflectable between raised and lowered positions of the lugs relative to the opening. The lugs are coextensive, the fingers are coextensive, and there are supporting feet formed in the lower face of the frame.

According to the principle of the invention a drying rack and contact lens storage case assembly includes a contact lens storage case assembly consisting of an integral base formed with an externally threaded first receptacle having a first inner diameter and an opposed externally threaded second receptacle having a second inner diameter equal to the first inner diameter of the first receptacle, and internally threaded first and second caps relating to the first and second receptacles, respectively, the first cap having a third inner diameter, the second cap having a fourth inner diameter equal to the third inner diameter of the first cap, and the third and fourth diameters of the first and second caps each being somewhat larger than each of the first and second diameters of the first and second receptacles, respectively. A frame has opposed upper and lower faces. First, second, third, and fourth drying structures are formed in the frame. Each of the first, second, third, and fourth drying structures include an opening formed through the frame from the upper face to the lower face, the opening having geometric center and a width greater than each of the first, second, third, and fourth inner diameters of the contact lens storage case assembly, and fingers formed in the frame, the fingers extending into the opening toward the geometric center and terminating with free ends located between the width and the geometric center of the opening, the free ends of each of the fingers formed with a lug projecting upwardly relative to the upper face of the frame, and the lugs being located between the width and the geometric center of the opening and residing in a region that is less than each of the first, second, third, and fourth inner diameters of the contact lens storage case assembly. The first and second receptacles of the base of the contact lens storage case assembly are concurrently deposited over the upper face of the frame on the fingers of the first and second drying structures, respectively, the first cap is deposited over the upper face of the frame on the fingers of the third drying structure, and the second cap is deposited over the upper face of the frame on the fingers of the fourth drying structure. The lugs of the first drying structure extend into the first receptacle within the first inner diameter of the first receptacle, the lugs of the second drying structure extend into the second receptacle within the second inner diameter of the second receptacle, the lugs of the third drying structure extend into the first cap within the third inner diameter of the first cap, the lugs of the fourth drying structure extend into the second cap within the fourth inner diameter of the second cap, and the openings of the first, second, third, and fourth drying structures provide drying ventilation for the first receptacle, the second receptacle, the first cap, and the second cap, respectively. The fingers of each of the first, second, third, and fourth drying structures are flexurally deflectable between raised and lowered positions of the lugs relative to the opening. The lugs are coextensive, the fingers are coextensive, and there are supporting feet formed in the lower face of the frame.

BRIEF DESCRIPTION OF THE DRAWINGS

Referring to the drawings:

FIG. 1 is a top perspective view of a drying rack and contact lens storage case assembly including a drying frame, and a contact lens storage case assembly shown disassembled and spaced from the drying frame in preparation for installation to drying frame for storage and drying purposes;

FIG. 2 is a bottom perspective view of the embodiment of FIG. 1;

FIG. 6 is an exploded perspective view of an alternate embodiment of a drying rack assembly for a contact lens storage case assembly;

FIG. 7 is a view similar to that of FIG. 6 illustrating the drying rack assembly as it would appear assembled;

FIG. 8 is a section view taken along line 8-8 of FIG. 7;

FIG. 13 is a top perspective view of a contact lens storage case assembly drying rack constructed and arranged in accordance with still another alternate embodiment of the invention;

FIG. 14 is a section view taken along line 14-14 of FIG. 13;

FIG. 15 is a bottom perspective view of the embodiment of FIG. 13;

FIG. 16 is a top plan view of the embodiment of FIG. 13;

FIG. 17 is a view similar to that of FIG. 13 illustrating a contact lens storage case assembly as it would appear installed onto the drying rack;

FIG. 18 is as top plan view of the embodiment of FIG. 17 depicting the contact lens storage case assembly in phantom outline for illustrative purposes; and FIG. 19 is a section view taken along line 19-19 of FIG. 18.

DETAILED DESCRIPTION

Figure 3:
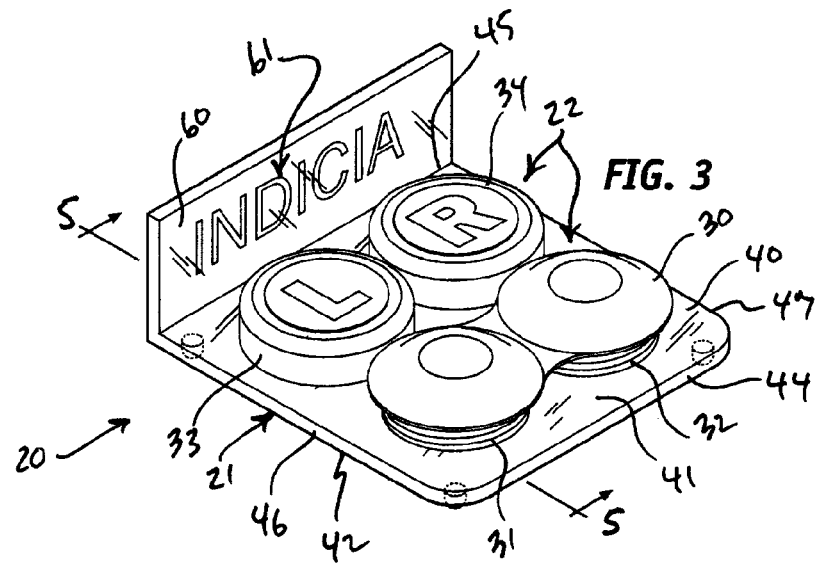
FIG. 3 is a view similar to that of FIG. 1 illustrating the contact lens storage case assembly as it would appear installed with respect to the drying frame.

Turning now to the drawings, in which like reference characters indicate corresponding elements throughout the several views, attention is first directed to FIGS. 1 and 2 illustrating a drying rack and contact lens storage case assembly 20 including a drying frame denoted generally at 21, and a contact lens storage case assembly denoted generally at 22. Contact lens storage case assembly 22 is standard, common, and well known, and consists of a conventionally formed base 30, formed opposed, spaced-apart receptacles 31 and 32, and a pair of conventionally formed lids or caps 33 and 34 relating to receptacles 31 and 32, respectively. Base 30 and caps 33 and 34 are each integrally formed of plastic as is the case with standard contact lens storage case assemblies, such as assembly 22. Receptacles 31 and 32 are externally threaded, and caps 33 and 34 are internally threaded. In particular, receptacles 31 and 32 have outer diameters D1 and D2, respectively, which are externally threaded, and caps 33 and 34 having inner diameters D3 and D4, respectively, which are internally threaded and which encircle the interior volumes of caps 33 and 34, respectively. Receptacles 31 and 32 also have inner diameters D5 and D6 which encircle the interior volumes of receptacles 31 and 32, respectively. Receptacles 31 and 32 are equal in size and shape, outer diameter D1 of receptacle 31 is equal to outer diameter D2 of receptacle 32, and inner diameter D5 of receptacle 31 is equal to inner diameter D6 of receptacle 32. Outer diameters D1 and D2 of receptacles 31 and 32 are somewhat greater or larger than inner diameters D5 and D6 of receptacles 31 and 32, respectively. Caps 33 and 34 are equal in size and shape, and inner diameter D3 of cap 33 is equal to inner diameter D4 of cap 34.

Contact lens storage case assembly 22 is used to keep and store a pair of contact lens during periods of nonuse, such as during the night. In use, receptacles 31 and 32 are each filled with a suitable contact lens solution, left and right contact lens are set into the respective receptacles 31 and 32, and the internally threaded inner diameters D3 and D3 of caps 33 and 34 are tightly threaded onto outer diameters D1 and D2 of receptacles 31 and 32 to enclose and seal the contents of receptacles 31 and 32. The contact lens solution in receptacles 31 and 32 keeps the respective contact lenses moist. To use the contact lens, caps 33 and 34 are removed from receptacles 31 and 32, and the contact lens are removed from receptacles 31 and 32 and applied to the user's eyes. At this point, it is important to thoroughly clean and dry contact lens storage case assembly 22. To clean receptacles 31 and 32 and caps 33 and 34, any solid matter or debris is removed from the respective sections, and the respective sections are thoroughly rinsed with hot water or with a contact lens solution. After this cleaning, the contact lens storage case assembly is thoroughly dried and stored with the use of drying frame 21 until the next use of contact lens storage case assembly 22.

To permit the inner diameters D3 and D4 of caps 33 and 34 to be threaded onto outer diameters D1 and D2 of receptacles 31 and 32, the inner diameters D3 and D4 are somewhat greater or larger than outer diameters D1 and D2 of receptacles 31 and 32, respectively. Because outer diameters D1 and D2 of receptacles 31 and 32 are somewhat greater or larger than inner diameters D5 and D6 of receptacles 31 and 32, inner diameters D3 and D4 of caps 33 and 34 are somewhat greater or larger than inner diameters D5 and D6 of receptacles 31 and 32, respectively.

Set forth for the purpose of orientation and reference, contact lens storage case assembly 22 is generally representative of a standard-sized and conventional contact lens storage case assembly. Accordingly, further details of contact lens storage case assembly 22 are well known to the skilled artisan and will not be discussed in further detail.

Figure 4:
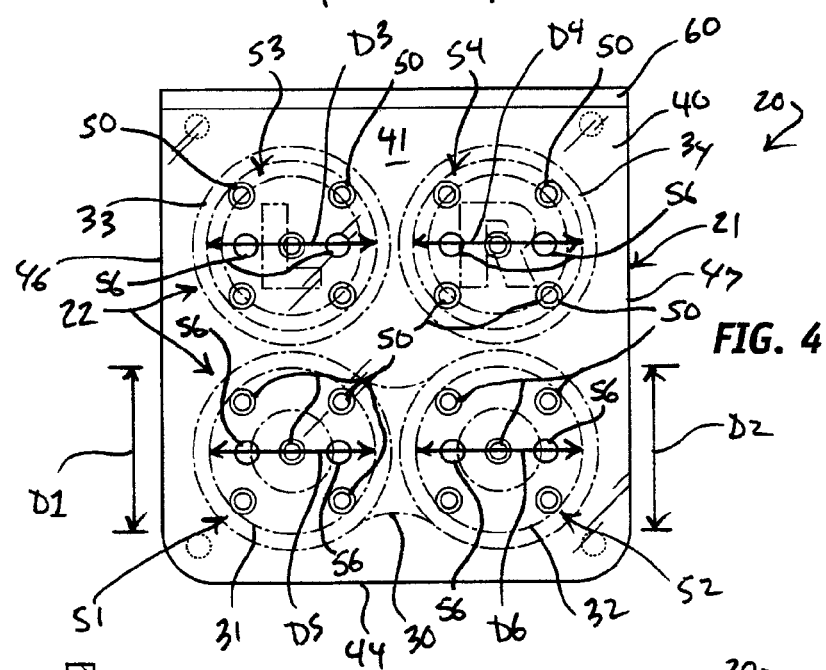
FIG. 4 is as top plan view of the embodiment of FIG. 3 depicting the contact lens storage case assembly in phantom outline for illustrative purposes.

According to the principle of the invention, and with reference in relevant part to FIGS. 1-5, drying frame 21 is preferably formed of plastic or other strong, resilient material or combination of materials, is preferably integrally formed, such as through molding or machining, and consists of a broad, flat body 40 that is generally square in shape and which has opposed, parallel upper and lower faces 41 and 42, and a marginal perimeter extremity or edge formed by opposed, parallel front and rear end edges 44 and 45 having substantially equal lengths, and opposed parallel side edges 46 and 47 extending therebetween, and which also have substantially equal lengths. Upper face 41 is formed with upstanding hubs or protuberances 50, and lower face 42 is formed with spaced apart supporting feet 48 illustrated in FIG. 2, which may be directed against a support surface to support drying frame 21 at an elevated location relative to the support surface. Protuberances 50 are substantially equal in size and shape, and project upward from upper face 41. According to the principle of the invention, protuberances are arranged in discrete clusters or patterns 51, 52, 53, and 54. In the present embodiment, there are twenty protuberances 50, and patterns 51, 52, 53, and 54 each have five of the twenty protuberances, which are equidistantly spaced apart and include one protuberance 50 encircled by a pattern of four protuberances 50 as best shown in FIGS. 1 and 4. Patterns 51, 52, 53, and 54 of protuberances 50 are formed within the perimeter edge of body 40, such that the marginal perimeter edge of body 40 encircles patterns 51, 52, 53, and 54 of protuberances. Ventilation openings 56 are formed through body 40 of drying frame 21 from lower face 42 to upper face 41 within each of the patterns 51-54 of protuberances to provide drying ventilation at patterns 51-54 of protuberances 50. In the present embodiment, patterns 51-54 of protuberances 50 are each associated with two ventilation openings 56, and less or more ventilation openings 56 may be incorporated in conjunction with each of patterns 51-54 if so desired.

Patterns 51 and 52 of protuberances 50 are spaced apart, and are formed proximate to front edge 44 of body 40 between side edges 46 and 46 of body 40. Patterns 53 and 54 of protuberances 50 are generally parallel with respect to patterns 51 and 52 of protuberances 50. Patterns 53 and 54 of protuberances 50 are spaced apart, and are formed proximate to rear edge 45 of body 40 between side edges 46 and 47 of body 50. According to the principle of the invention, patterns 51 and 52 of protuberances 50 relate to receptacles 31 and 32, respectively, formed in base 30, and patterns 53 and 54 of protuberances 50 relate to caps 33 and 34, respectively. In a further and more specific aspect, patterns 51 and 52 of protuberances 50 relate to and are able to be received by inner diameters D5 and D6 of receptacles 31 and 32, respectively, and patterns 53 and 54 of protuberances relate to and are able to be received by inner diameters D3 and D4 of caps 33 and 34.

For storage and drying purposes, drying frame 21 is set onto a support surface, such as a counter, by directing feet 48 against the support surface such that upper face 41 directed upwardly orienting drying frame 21 for use in receiving and holding base 30 and caps 33 and 34 for storage and drying purposes, such as after cleaning and rinsing. Receptacles 31 and 32 of base 30 are concurrently positionable over and on patterns 51 and 52 of protuberances 50, cap 33 is positionable over and on pattern 53 of protuberances 50, and cap 34 is positionable over and on pattern 54 of protuberances 50. The installation of base 30 and caps 33 and 34 to drying frame 21 is shown in FIG. 3 and also FIG. 4. For illustrative purpose, base 30 and caps 33 and 34 of FIG. 4 are depicted in phantom outline to illustrate the relationship between patterns 51-54 of protuberances 50 and the corresponding inner diameters of receptacles 31 and 32 of base 30, and caps 33 and 34.

Figure 5:
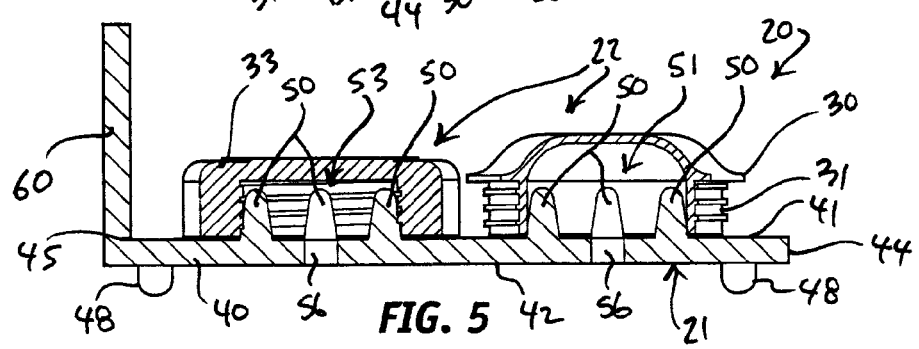
FIG. 5 is a section view taken along line 5-5 of FIG. 3.

With respect to the installation of base 30 to drying frame 21, pattern 51 of protuberances 50 is to extend into the interior volume of receptacle 31 as shown in FIG. 5 and the pattern of four protuberances 50 encircling the fifth protuberance 50 of pattern 51 are positioned and spaced relative to each other to concurrently relate to inner diameter D5 and is to be received against inner diameter D5 of receptacle 31 as illustrated in FIG. 4 to hold and secure receptacle 31 for storage and drying purposes, and identically pattern 52 of protuberances 50 is to extend into the interior volume of receptacle 32 and the pattern of four protuberances 50 encircling the fifth protuberance 50 of pattern 52 are positioned and spaced relative to each other to concurrently relate to inner diameter D6 and is to be received against inner diameter D6 of receptacle 32 as seen in FIG. 4 to hold and secure receptacle 32 for storage and drying purposes. With respect to the installation of caps 33 and 34 to drying frame 21, pattern 53 of protuberances 50 is to extend into the interior volume of cap 33 as shown in FIG. 5 and the pattern of four protuberances 50 encircling the fifth protuberance 50 of pattern 53 are positioned and spaced relative to each other to concurrently relate to inner diameter D3 and is to be received against inner diameter D3 of cap 33 as seen in FIG. 4 to hold and secure cap 33 for storage and drying purposes, and identically pattern 54 of protuberances 50 is to extend into the interior volume of cap 34 and the pattern of four protuberances 50 encircling the fifth protuberance 50 of pattern 54 are positioned and spaced relative to each other to concurrently relate to inner diameter D4 and is to be received against inner diameter D4 of cap 34 as shown in FIG. 4 to hold and secure cap 34 for storage and drying purposes.

To install base 30 to drying frame 21 for storage and drying purposes, base 30 is inverted over patterns 51 and 52 of protuberances 50 as seen in FIG. 1 registering receptacles 31 and 32 with patterns 51 and 52 of protuberances and base 30 is presented downwardly onto upper face 41 of body 40 applying pattern 51 of protuberances 50 into the interior volume of receptacle 31 as shown in FIG. 5 and the four protuberances 50, which is a pattern of protuberances, encircling the fifth protuberance 50 of pattern of pattern 51 are concurrently received against inner diameter D5 of receptacle 31 as illustrated in FIG. 4 to hold and secure receptacle 31 for storage and drying purposes, and identically pattern 52 of protuberances 50 is concurrently applied into the interior volume of receptacle 32 and the four protuberances 50, which is a pattern of protuberances, encircling the fifth protuberance 50 of pattern of pattern 52 are concurrently received against inner diameter D6 of receptacle 32 as seen in FIG. 4 to hold and secure receptacle 32 for storage and drying purposes. This application of receptacles 31 and 32 of base 30 over and onto patterns 51 and 52 of protuberances 50 installs base 30 to drying frame 21 for storage and drying purposes, and ventilation openings 56 formed in patterns 51 and 52 provide drying ventilation for receptacles 31 and 32 of base 30.

To install cap 33 to drying frame 21, cap 33 is inverted over pattern 53 of protuberances 50 as seen in FIG. 1 registering cap 33 with pattern 53 of protuberances and cap 33 is presented downwardly onto upper face 41 of body 40 applying pattern 53 of protuberances 50 into the interior volume of cap 33 as shown in FIG. 5 and the four protuberances 50, which is a pattern of protuberances, encircling the fifth protuberance 50 of pattern 53 are concurrently received against inner diameter D3 of cap 33 as illustrated in FIG. 4 to hold and secure cap 33 for storage and drying purposes. This application of cap 33 over and onto pattern 53 of protuberances 50 installs cap 33 to drying frame 21 for storage and drying purposes, and ventilation openings 56 formed in pattern 53 provide drying ventilation for cap 33. To install cap 34 to drying frame 21, cap 34 is inverted over pattern 54 of protuberances 50 as seen in FIG. 1 registering cap 34 with pattern 54 of protuberances and cap 34 is presented downwardly onto upper face 41 of body 40 applying pattern 54 of protuberances 50 into the interior volume of cap 34 and the four protuberances 50, which is a pattern of protuberances, encircling the fifth protuberance 50 of pattern of pattern 54 are concurrently received against inner diameter D4 of cap 34 as illustrated in FIG. 4 to hold and secure cap 34 for storage and drying purposes. This application of cap 34 over and onto pattern 54 of protuberances 50 installs cap 34 to drying frame 21 for storage and drying purposes, and ventilation openings 56 formed in pattern 54 provide drying ventilation for cap 34. The spacing of patterns 51-54 of protuberances 50 permits base 30 and caps 33 and 34 to be concurrently applied to body 40 of drying frame 21 for storage and drying purposes. To remove base 30 and caps 33 and 34 from drying frame 21, each need only be taken up, such as by hand, and lifted away from upper face 41 of drying frame 21.

To distinguish and identify drying frame 21 as relating to particular user to prevent or otherwise inhibit unauthorized use of drying frame 21, drying frame 21 is formed with an upstanding support 60. Support 60 is attached to a length of the marginal perimeter edge of body 40, which, in this instance, is the length of rear edge 45 of body 40. In the present embodiment, support 60 is integrally formed with body 40, and projects upright from rear edge 45 relative to upper face 41 of body 40. Indicia 61 applied to support 60 consists of distinguishing markings, signs, or indications, which are designed to distinguish and identify drying frame 21 as relating to a particular user to prevent unauthorized use of drying frame 21 and to prevent unauthorized or unintended use of a contact lens storage case assembly installed onto drying frame 21 for storage and drying purposes. Indicia 61 can be a name, a word, a sign, a symbol, a color, a series of colors, or the like to provide the desired identification to prevent unauthorized or unintended use of drying frame 21 and/or a contact lens storage case assembly installed on drying frame 21.

FIG. 6 is an exploded perspective view of an alternate embodiment of a drying rack assembly 70 for a contact lens storage case assembly, such as contact lens storage case assembly 22. In common with assembly 20, assembly 70 shares drying frame 21, including base 40 formed with supporting feet 48 formed in lower face 42, patterns 51-54 of protuberances 50 formed in upper face 41, and ventilation openings 56. In assembly 70 there is a support platform 75. Support platform 75 is preferably formed of plastic or other strong, resilient material or combination of materials, is preferably integrally formed, such as through molding or machining, and consists of a broad, flat body 80 that is larger than body 40 discussed above and that is generally square in shape and which has opposed, parallel upper and lower faces 81 and 82, and a marginal perimeter extremity or edge formed by opposed, parallel front and rear end edges 84 and 85 having substantially equal lengths, and opposed parallel side edges 86 and 87 extending therebetween, and which also have substantially equal lengths. Upper face 81 is formed with recesses 90 arranged to concurrently accept supporting feet 48 formed in the lower face of drying frame 21 as substantially shown in FIGS. 78 and 8 to provide a convenient holder for drying frame 21, and lower face 82 is formed with spaced apart supporting feet 88 (FIG. 8), which may be directed against a support surface to support drying frame 21 at an elevated location relative to the support surface. Ventilation openings 90 are formed through body 80 of support platform 75 from lower face 82 to upper face 81 to provide drying ventilation for drying frame 21 set onto body 80 as illustrated in FIGS. 7 and 8. In the present embodiment there are eight ventilation openings 90 formed in body 80, and less or more may be provided if so desired.

To distinguish and identify support platform 75 of assembly 70, including drying frame 21 installed on support platform 75 and a contact lens storage case assembly installed on drying frame 21, as relating to particular user to prevent or otherwise inhibit unauthorized use of assembly 70, support platform 75 is formed with an upstanding support 100. Support 100 is attached to a length of the marginal perimeter edge of body 80, which, in this instance, is the length of rear edge 85 of body 80. In the present embodiment, support 100 is integrally formed with body 80, and projects upright from rear edge 85 relative to upper face 81 of body 80. Indicia 101 applied to support 100 consists of distinguishing markings, signs, or indications, which are designed to distinguish and identify support platform 75 as relating to a particular user to prevent unauthorized or unintended use of assembly 70, including support platform 75, drying frame 21 installed on support platform 75, and a contact lens storage case assembly installed on drying frame 21 for storage and drying purposes. Indicia 101 can be a name, a word, a sign, a symbol, a color, a series of colors, or the like to provide the desired identification to prevent the unauthorized or unintended use as described above.

Figure 9:
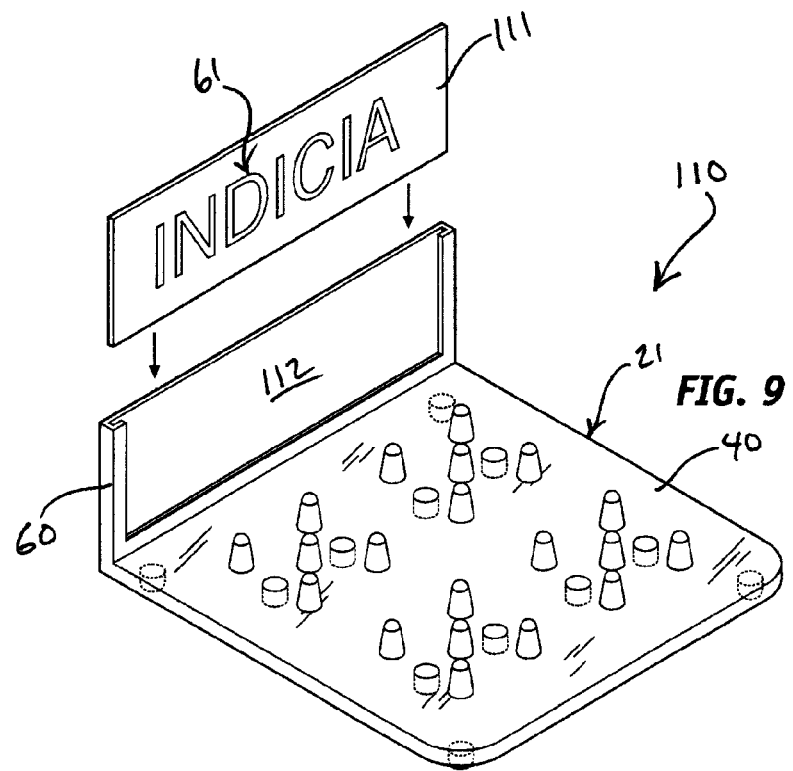
FIG. 9 is an exploded perspective view of yet another alternate embodiment of a drying rack assembly for a contact lens storage case assembly.
Figure 10:
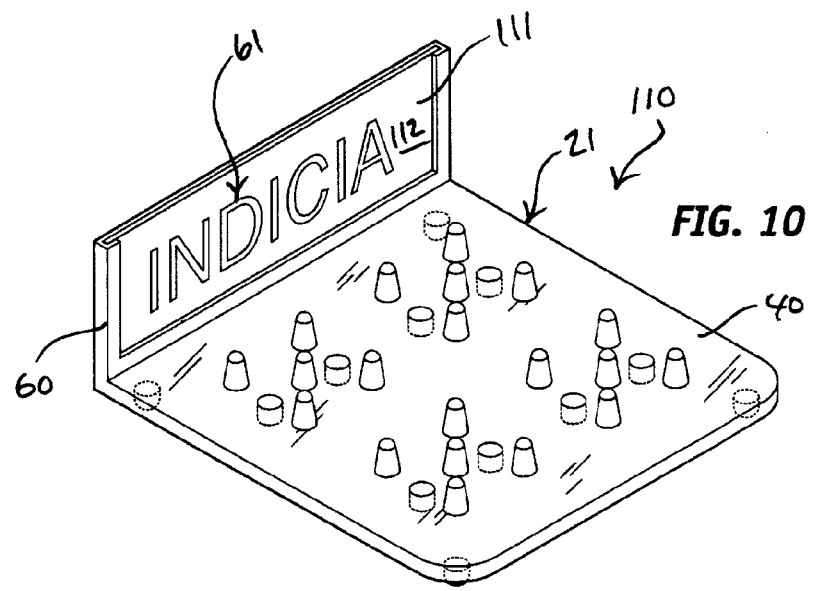
FIG. 10 is a view similar to that of FIG. 9 illustrating the drying rack assembly as it would appear assembled.

Attention is now directed to FIGS. 9 and 10 illustrating yet another embodiment of a drying rack assembly 110 for a contact lens storage case assembly. In common with assembly 70, assembly 110 shares drying frame 21 including body 40 and all related components, support 60, and indicia 61. In assembly 110, indicia 61 is carried by or otherwise formed in a plate 111, which is formed of metal, plastic, or the like. In assembly 110, indicia 61 are applied to plate 111, which is carried by support 60 as shown in FIG. 10. Plate 111 is a separate and discreet component relative to support 60, and is removably coupled to support 60 and is, moreover, movable between a first position detached from support 60 as shown in FIG. 9, and a second position attached to and thus carried by support 60 as shown in FIG. 10. In the present embodiment, support 60 is formed with a sleeve 112 to accept and hold plate 112 as illustrated in FIG. 10. The instruction provided by assembly 110 is to demonstrate indicia 61 carried by a plate 111 removably couplable to support 60, which allows plate 111 and indicia 61 carried thereby to be removed for cleaning or replacement as may be required.

Figure 11:
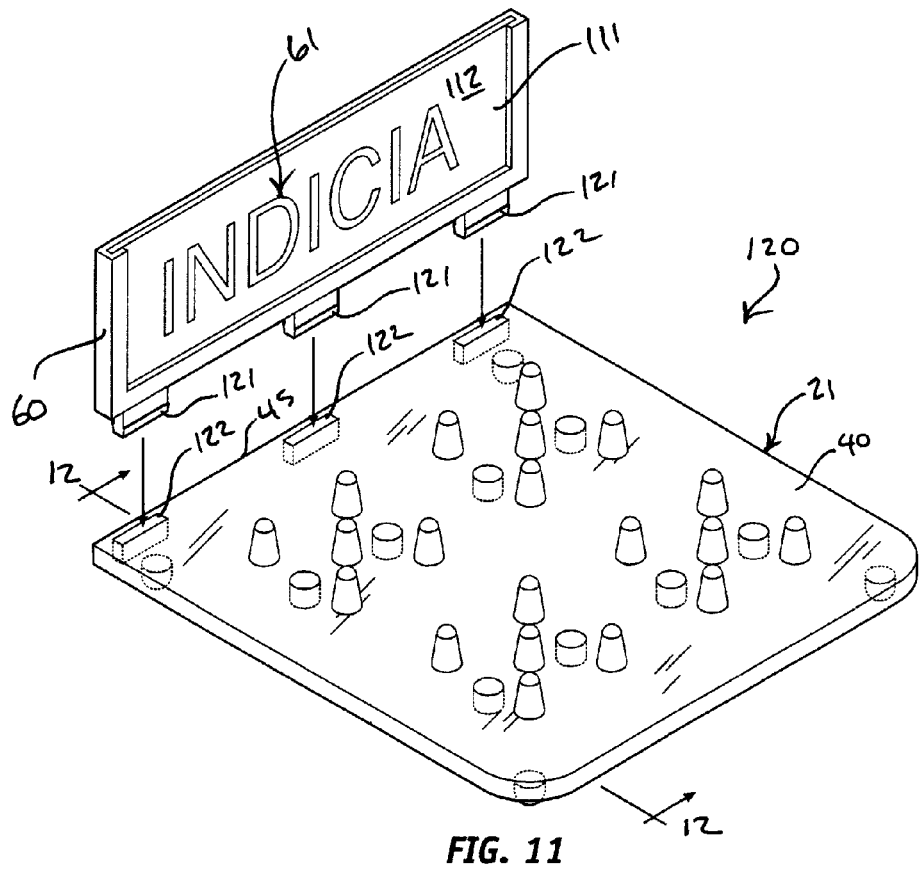
FIG. 11 is a partially exploded perspective view of a further another alternate embodiment of a drying rack assembly for a contact lens storage case assembly.
Figure 12:
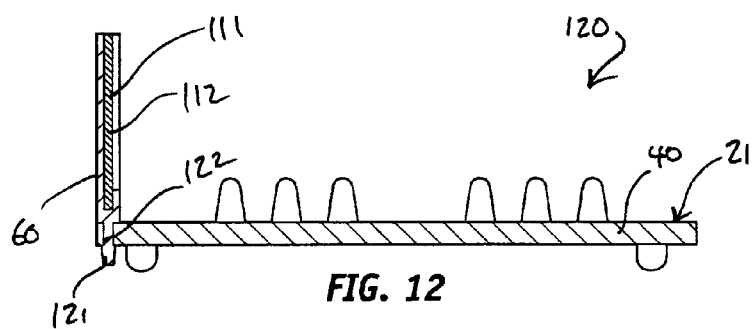
FIG. 12 is a section view taken along line 12-12 of FIG. 11 illustrating the drying rack assembly as it would appear assembled.

In assembly 110 shown in FIGS. 9 and 10, support 60 is integrally formed with base 40. If desired, support 60 may be removably attached to base 40 in an alternate embodiment of a drying rack assembly 120 for a contact lens storage case assembly as shown in FIGS. 11 and 12. In common with assembly 110, assembly 111 shares drying frame 21 including body 40 and all related components, support 60, and indicia 61 carried by plate 111 removably applied to sleeve 112 formed in support 60. In assembly 111, support 60 is a separate and discrete component with respect to body 40, and is removably couplable or otherwise engagable to body 40 with an engagement assembly including elements 121 thereof formed in support 60 which are detachably engagable to corresponding complemental or complementing elements thereof formed in body 40 along rear edge 45. In the present embodiment, elements 121 are male engagement elements or tabs that relate to and are removably received by corresponding slots formed in body 40 forming the corresponding complemental or complementing engagement elements of the engagement assembly formed between support 60 and body 40. FIG. 11 illustrates support 60 as it would appear detached from body 40, and FIG. 12 is a section view illustrating support 60 as it would appear coupled to body 40, and further illustrating a tab forming one of the engagement elements 121 as it would appear received into and through one of a corresponding slot forming one of the corresponding complemental or complementing engagement elements. Although elements 121 are carried by body 60 and corresponding complemental or complementing elements 122 are carried by body 40, this arrangement can be reversed or mixed and matched as may be desired. Furthermore, other engagement assemblies suitable to provide a removable or releasable attachment of support 60 to body 40 can be used without departing from the invention.

Reference is now made to FIG. 13, which is a top perspective of a contact lens storage case assembly drying rack 200 constructed and arranged in accordance with still another alternate embodiment of the invention. Rack 200 is useful in conjunction with contact lens storage case assembly 22 illustrated in FIG. 17, FIG. 18, and FIG. 19. For reference purposes in connection with the ensuing discussion of rack 200, and referring to FIGS. 17-19 in relevant part, contact lens storage case assembly 22 includes base 30 having opposed, spaced-apart receptacles 31 and 32, and lids or caps 33 and 34 relating to receptacles 31 and 32, respectively. Receptacles 31 and 32 are externally threaded, and caps 33 and 34 are internally threaded. As referenced in FIG. 18, receptacles 31 and 32 have outer diameters D1 and D2, respectively, which are externally threaded, and caps 33 and 34 having inner diameters D3 and D4, respectively, which are internally threaded and which encircle the interior volumes of caps 33 and 34, respectively. Receptacles 31 and 32 also have inner diameters D5 and D6 which encircle the interior volumes of receptacles 31 and 32, respectively. Receptacles 31 and 32 are equal in size and shape, outer diameter D1 of receptacle 31 is equal to outer diameter D2 of receptacle 32, and inner diameter D5 of receptacle 31 is equal to inner diameter D6 of receptacle 32. Outer diameters D1 and D2 of receptacles 31 and 32 are somewhat greater or larger than inner diameters D5 and D6 of receptacles 31 and 32, respectively. Caps 33 and 34 are equal in size and shape, and inner diameter D3 of cap 33 is equal to inner diameter D4 of cap 34. To permit the inner diameters D3 and D4 of caps 33 and 34 to be threaded onto outer diameters D1 and D2 of receptacles 31 and 32, the inner diameters D3 and D4 are somewhat greater or larger than outer diameters D1 and D2 of receptacles 31 and 32, respectively. Because outer diameters D1 and D2 of receptacles 31 and 32 are somewhat greater or larger than inner diameters D5 and D6 of receptacles 31 and 32, inner diameters D3 and D4 of caps 33 and 34 are somewhat greater or larger than inner diameters D5 and D6 of receptacles 31 and 32, respectively. The utility of contact lens storage case assembly 22 is as previously described.

According to the principle of the invention, and with reference in relevant part to FIGS. 13, 15, 16, 18, and 19, rack 200 consists of a drying frame 201 formed of plastic or other strong, resilient material or combination of materials, and which is preferably integrally formed, such as through molding or machining. Frame 201 is a broad, flat plate or body that is generally square in shape and which has opposed, parallel upper and lower faces 211 and 212, and a marginal perimeter extremity or edge formed by opposed, parallel front and rear end edges 214 and 215 having substantially equal lengths, and opposed parallel side edges 216 and 217 extending therebetween, and which also have substantially equal lengths. Lower face 212 is formed with spaced apart supporting feet 218, which may be directed against a support surface to support rack 200 at an elevated location relative to the support surface, such as a countertop surface, vanity surface, or the like. Drying structures 221-224 are formed in frame 201. Drying structures 221-224 are identical in every respect. Accordingly, the details of drying structure 221 will now be discussed in detail, with the understanding that the ensuing discussion of drying structure 232 applies equally to each of drying structures 222-224.

Drying structure 221 consists of an opening 230 formed through frame 201 from upper face 211 to lower face 212. Opening 230 is defined and bound by a perimeter edge 231 of frame 201. As referenced in FIGS. 16 and 18, opening 230 has a geometric center C and a diameter or width W, which is greater than each of inner diameters D3 and D4 of caps 33 and 34, and each of inner diameters D5 and D6 of receptacles 31 and 32, respectively.

Drying structure 221 is formed with fingers 240. Fingers 240 are formed in frame 210, and extend into opening 230 from perimeter edge 231 bounding opening 230 toward geometric center C, and terminate with free ends 241, which are located between geometric center C of opening 230 and the width W of opening 230 defined by perimeter edge 231. Because perimeter edge 231 defines width W of opening 230, according to this disclosure fingers 240 extend into opening 230 from width W of opening 230 to free ends 241 located between geometric center C of opening 230 and width W of opening 230. Free ends 241 of fingers 240 encircle geometric center C of opening 230, and are each formed with an upstanding protuberance or lug 242. Lugs 242 project or otherwise extending upwardly from free ends 241 of corresponding fingers 240, and further project or otherwise extend upwardly relative to upper face 221 of frame 201. Like free ends 241 of fingers 240, lugs 242 carried by free ends 241 of fingers 240 are located at opening 230, and are located between geometric center C of opening 230 and the width W of opening 230 defined by perimeter edge 231. Because perimeter edge 231 defines width W of opening 230, according to this disclosure lugs 242 are located between geometric center C of opening 230 and width W of opening 230. Like free ends 241 of fingers 240, lugs 242 further encircle geometric center C of opening 230. Free ends 241 of fingers 240 and lugs 242 carried by free ends 241 of fingers 240 reside along a diameter or region that is less than or otherwise within each of inner diameters D3 and D4 of caps 33 and 34, and each of inner diameters D5 and D6 of receptacles 31 and 32, respectively, as clearly shown in FIG. 18.

Fingers 240 are equal in size and shape and are thus coextensive with respect to each other. Lugs 242 are likewise equal in size and shape and are thus coextensive with respect to each other. Fingers 240 are also flexurally deflectable or otherwise movable relative to frame 201 between raised and lowered positions of lugs 242 relative to opening 230 as illustrated in FIG. 14. Each finger 240 and corresponding lug 242 pair is considered a finger structure, and these finger structures are identical to each other in every respect. In the present embodiment, drying structure 221 incorporates four finger structures, namely, four finger 240 and lug 242 pairs. In drying structure 221, the described finger structures are equidistant relative to each other, encircle geometric center C, extending inwardly into opening 230 toward geometric center C, and are arranged in two diametrically opposing pairs. Although drying structure 221 incorporates four finger structures, namely, four finger 240 and lug 242 pairs, drying structure 221 may incorporate less or more such finger structures, such as two finger structures, three finger structures, five finger structures, or other selected number of finger structures. In drying structure 221, the described finger structures are equidistant relative to each other, encircle geometric center C, extending inwardly into opening 230 toward geometric center C, and are arranged in two diametrically opposing pairs.

According to the principle of the invention, lugs 242 of drying structures 221-224 are arranged in clusters or patterns 251, 252, 253, and 254. In the present embodiment, patterns 251, 252, 253, and 254 are spaced apart relative to each other and each have four finger structures and thus four fingers 240 and four corresponding lugs 242, and patterns 251, 252, 253, and 254 each relate to an opening 230. Patterns 251 and 252 of lugs 242 of drying structures 221 and 222 are spaced apart, and are formed proximate to front edge 214 of frame 201 between side edges 216 and 217 of frame 201. Patterns 253 and 254 of lugs 242 of drying structures 223 and 224 are generally parallel with respect to patterns 251 and 252 of lugs 242 of drying structures 221 and 222, and are formed proximate to rear edge 215 of frame 201 between side edges 216 and 217 of frame 201. According to the principle of the invention, patterns 251 and 252 of lugs 242 of drying structures 221 and 222 relate to receptacles 31 and 32, respectively, formed in base 30, and patterns 253 and 254 of lugs 242 of drying structures 223 and 224 relate to caps 33 and 34, respectively. In a further and more specific aspect, patterns 251 and 252 of lugs 242 of drying structures 221 and 222 relate to and are able to be received within inner diameters D5 and D6 of receptacles 31 and 32, respectively, and patterns 253 and 24 of lugs 242 of drying structures 223 and 224 relate to and are able to be received within inner diameters D3 and D4 of caps 33 and 34.

For storage and drying purposes, rack 200 is set onto a support surface, such as a counter, by directing feet 218 against the support surface such that upper face 211 is directed upwardly orienting rack 200 for use in receiving and holding base 30 and caps 33 and 34 for storage and drying purposes as shown in FIG. 19, such as after cleaning and rinsing. Receptacles 31 and 32 of base 30 are concurrently positionable over upper face 211 of frame 201 and over patterns 251 and 252 of lugs 242 of drying structures 221 and 222, cap 33 is positionable over upper face 211 of frame 201 and over pattern 253 of lugs 242 of drying structure 223, and cap 34 is positionable over upper face 211 of frame 201 and over pattern 254 of lugs 242 of drying structure 224. The installation of base 30 and caps 33 and 34 to rack 200 is shown in FIGS. 17 and 18. For illustrative purposes, base 30 and caps 33 and 34 of FIG. 18 are depicted in phantom outline to illustrate the relationship between patterns 251-254 of lugs 242 of drying structures 221-224 and the corresponding inner diameters of receptacles 31 and 32 of base 30, and caps 33 and 34.

In the installation of base 30 to rack 200 for drying purposes, base 30 is inverted and positioned over and atop upper face 211 of frame 201, receptacle 31 is positioned over and atop and also directly against fingers 240 of drying structure 221 so as to be in direct contact with fingers 240 of drying structure 221 as shown in FIG. 19, receptacle 32 is identically positioned over and atop and also directly against fingers 240 of drying structure 222 so as to be in direct contact with fingers 240 of drying structure 222, pattern 251 of lugs 242 of drying structure 221 extend into the interior volume of receptacle 31 as shown in FIG. 19 within inner diameter D5, and identically pattern 252 of lugs 242 of drying structure 222 extend into the interior volume of receptacle 32 within inner diameter D6. This application of receptacles 31 and 32 of base 30 over patterns 251 and 252 of lugs 242 of drying structures 221 and 222 installs base 30 to frame 201 of rack 200 for storage and drying purposes, and openings 230 of drying structures 221 and 222 relating to patterns 251 and 252 of lugs 242 of drying structures 221 and 222, respectively, provide exemplary drying ventilation for receptacles 31 and 32 of base 30. In the installation of base 30 onto rack 200, receptacles 31 and 32 are supported directly against and atop so as to be in direct contact with the fingers 240 of the corresponding drying structures 221 and 222 that define spaced-apart contact points between receptacles 31 and 32 and rack 200, and this application of receptacles 31 and 32 onto the spaced-apart contact points defined by fingers 240 of drying structures 221 and 222 defines a discontinuous contact between base 30 and rack that minimizes contact between base 30 and rack 200 to facilitate exemplary drying of base 30, in accordance with the principle of the invention. Furthermore, with base 30 so installed onto rack 200 as herein specifically described, lugs 242 of the corresponding fingers 240 of drying structures 221 and 222 are positioned so as to confront and interact with inner diameters D5 and D6 of receptacles 31 and 32 to prevent base 30 from inadvertently sliding off rack 200. After drying is complete, base 30 may simply be taken up by hand and lifted away from rack 200. Because fingers 240 of drying structures 221 and 222 are flexurally deflectable or otherwise movable relative to frame 201 between raised and lowered positions of lugs 242 relative to the corresponding openings 230 of drying structures 221 and 222 as previously discussed, the finger structures are free to deflect as may occur on the installation of base 30 to rack 200 so as to prevent the finger structures from breaking and to facilitate ease of installation.

In the installation of caps 33 and 34 to rack 200 for drying purposes, caps 33 and 34 are inverted and positioned over and atop upper face 211 of frame 201, cap 33 is positioned over and atop and also directly against fingers 240 of drying structure 223 so as to be in direct contact with fingers 240 of drying structure 223 as seen in FIG. 19, cap 34 is identically positioned over and atop and also directly against fingers 240 of drying structure 224 so as to be in direct contact with fingers 240 of drying structure 224, pattern 253 of lugs 242 of drying structure 223 extend into the interior volume of cap 33 as shown in FIG. 19 within inner diameter D3, and identically pattern 254 of lugs 242 of drying structure 224 extend into the interior volume of cap 34 within inner diameter D4. This application of caps 33 and 34 over patterns 253 and 254 of lugs 242 of drying structures 223 and 224 installs caps 33 and 34 to frame 201 of rack 200 for storage and drying purposes, and openings 230 of drying structures 221 and 222 relating to patterns 251 and 252 of lugs 242 of drying structures 221 and 222, respectively, provide drying ventilation for caps 33 and 34. In the installation of caps 33 and 34 onto rack 200, caps 33 and 34 are supported directly against and atop so as to be in direct contact with the fingers 240 of the corresponding drying structures 223 and 224 that define spaced-apart contact points between caps 33 and 34 and rack 200, and this application of caps 33 and 34 onto the spaced-apart contact points defined by fingers 240 of drying structures 223 and 224 defines a discontinuous contact between caps 33 and 34 and rack that minimizes contact between caps 33 and 34 and rack 200 to facilitate exemplary drying of caps 33 and 34, in accordance with the principle of the invention. Furthermore, with caps 33 and 34 so installed onto rack 200 as herein specifically described, lugs 242 of the corresponding fingers 240 of drying structures 223 and 224 are positioned so as to confront and interact with inner diameters D3 and D4 of caps 33 and 34 to prevent caps 33 and 34 from inadvertently sliding off rack 200. After drying is complete, caps 33 and 34 may simply be taken up by hand and lifted away from rack 200. Because fingers 240 of drying structures 223 and 224 are flexurally deflectable or otherwise movable relative to frame 201 between raised and lowered positions of lugs 242 relative to the corresponding openings 230 of drying structures 223 and 224 as previously discussed, the finger structures are free to deflect as may occur on the installation of caps 33 and 34 to rack 200 so as to prevent the finger structures from breaking and to facilitate ease of installation.

The present invention is described above with reference to preferred embodiments. However, those skilled in the art will recognize that changes and modifications may be made in the described embodiments without departing from the nature and scope of the present invention. Various changes and modifications to the embodiments herein chosen for purposes of illustration will readily occur to those skilled in the art. To the extent that such modifications and variations do not depart from the spirit of the invention, they are intended to be included within the scope thereof.

Having fully described the invention in such clear and concise terms as to enable those skilled in the art to understand and practice the same, the invention claimed is:

1. A drying rack and contact lens storage case assembly, comprising:
    a contact lens storage case assembly, including:
        an integral base formed with an externally threaded first receptacle having a first inner diameter, and an opposed externally threaded second receptacle having a second inner diameter equal to the first inner diameter of the first receptacle; and internally threaded first and second caps relating to the first and second receptacles, respectively, the first cap having a third inner diameter, the second cap having a fourth inner diameter equal to the third inner diameter of the first cap, and the third and fourth diameters of the first and second caps each being somewhat larger than each of the first and second diameters of the first and second receptacles, respectively;

a frame having opposed upper and lower faces;

first, second, third, and fourth drying structures formed in the frame, each of the first, second, third, and fourth drying structures comprising:

an opening through the frame from the upper face to the lower face, the opening having geometric center and a width greater than each of the first, second, third, and fourth inner diameters of the contact lens storage case assembly;

the frame having fingers, the fingers extending into the opening toward the geometric center and terminating with free ends located between the width and the geometric center of the opening, the free ends of each of the fingers formed with a lug projecting upwardly relative to the upper face of the frame, and the lugs being located between the width and the geometric center of the opening and residing in a region that is less than each of the first, second, third, and fourth inner diameters of the contact lens storage case assembly;

the first and second receptacles of the base of the contact lens storage case assembly concurrently positionable over the upper face of the frame on the fingers of the first and second drying structures, respectively, the first cap positionable over the upper face of the frame on the fingers of the third drying structure, and the second cap positionable over the upper face of the frame on the fingers of the fourth drying structure; wherein:

the lugs of the first drying structure to extend into the first receptacle within the first inner diameter of the first receptacle;

the lugs of the second drying structure to extend into the second receptacle within the second inner diameter of the second receptacle;

the lugs of the third drying structure to extend into the first cap within the third inner diameter of the first cap;

the lugs of the fourth drying structure to extend into the second cap within the fourth inner diameter of the second cap; and the openings of the first, second, third, and fourth drying structures to provide drying ventilation.

2. The drying rack and contact lens storage case assembly according to claim 1, wherein the fingers of each of the first, second, third, and fourth drying structures are flexurally deflectable between raised and lowered positions of the lugs relative to the opening.

3. The drying rack and contact lens storage case assembly according to claim 2, wherein the lugs are coextensive.

4. The drying rack and contact lens storage case assembly according to claim 3, wherein the fingers are coextensive.

5. A drying rack and contact lens storage case assembly according to claim 4, further comprising supporting feet formed in the lower face of the frame.

6. A drying rack and contact lens storage case assembly, comprising:

a contact lens storage case assembly, including:

an integral base formed with an externally threaded first receptacle having a first inner diameter, and an opposed externally threaded second receptacle having a second inner diameter equal to the first inner diameter of the first receptacle; and internally threaded first and second caps relating to the first and second receptacles, respectively, the first cap having a third inner diameter, the second cap having a fourth inner diameter equal to the third inner diameter of the first cap, and the third and fourth diameters of the first and second caps each being somewhat larger than each of the first and second diameters of the first and second receptacles, respectively;

a frame having opposed upper and lower faces;

first, second, third, and fourth drying structures formed in the frame, each of the first, second, third, and fourth drying structures comprising:

an opening through the frame from the upper face to the lower face, the opening having geometric center and a width greater than each of the first, second, third, and fourth inner diameters of the contact lens storage case assembly;

the frame having fingers, the fingers extending into the opening toward the geometric center and terminating with free ends located between the width and the geometric center of the opening, the free ends of each of the fingers formed with a lug projecting upwardly relative to the upper face of the frame, and the lugs being located between the width and the geometric center of the opening and residing in a region that is less than each of the first, second, third, and fourth inner diameters of the contact lens storage case assembly;

the first and second receptacles of the base of the contact lens storage case assembly concurrently deposited over the upper face of the frame on the fingers of the first and second drying structures, respectively, the first cap deposited over the upper face of the frame on the fingers of the third drying structure, and the second cap deposited over the upper face of the frame on the fingers of the fourth drying structure;

the lugs of the first drying structure extending into the first receptacle within the first inner diameter of the first receptacle;

the lugs of the second drying structure extending into the second receptacle within the second inner diameter of the second receptacle;

the lugs of the third drying structure extending into the first cap within the third inner diameter of the first cap;

the lugs of the fourth drying structure extending into the second cap within the fourth inner diameter of the second cap; and the openings of the first, second, third, and fourth drying structures provide drying ventilation for the first receptacle, the second receptacle, the first cap, and the second cap, respectively.

7. The drying rack and contact lens storage case assembly according to claim 6, wherein the fingers of each of the first, second, third, and fourth drying structures are flexurally deflectable between raised and lowered positions of the lugs relative to the opening.

8. The drying rack and contact lens storage case assembly according to claim 7, wherein the lugs are coextensive.

9. The drying rack and contact lens storage case assembly according to claim 8, wherein the fingers are coextensive.

10. A drying rack and contact lens storage case assembly according to claim 9, further comprising supporting feet formed in the lower face of the frame.

* * * * *